United States Patent [19]

Dobler et al.

[11] Patent Number: 4,778,531
[45] Date of Patent: Oct. 18, 1988

[54] EPIMERIZATION OF SUGARS, IN PARTICULAR OF D-ARABINOSE TO D-RIBOSE

[75] Inventors: Walter Dobler, Heidelberg; Hansgeorg Ernst, Ludwigshafen; Joachim Paust, Neuhofen, all of Fed. Rep. of Germany

[73] Assignee: BASF Aktiengesellschaft, Rheinland-Pfalz, Fed. Rep. of Germany

[21] Appl. No.: 68,171

[22] Filed: Jun. 30, 1987

[30] Foreign Application Priority Data

Jul. 5, 1986 [DE] Fed. Rep. of Germany ....... 3622643

[51] Int. Cl.$^4$ .............................. C07H 1/00; C13J 1/06
[52] U.S. Cl. .................................. 127/46.1; 127/46.3; 127/46.2; 127/48; 127/54; 127/55; 127/58; 536/1.1; 536/124; 204/186
[58] Field of Search .................... 127/46.1, 46.2, 46.3, 127/48, 54, 55, 58; 536/1, 124, 125; 204/186

[56] References Cited

U.S. PATENT DOCUMENTS

4,029,878  6/1977  Kruse ..................................... 536/1
4,355,158  10/1982 Wolf et al. ............................. 536/1
4,602,086  7/1986  Hiroshi et al. ....................... 536/125

FOREIGN PATENT DOCUMENTS

76894  6/1980  Japan.

OTHER PUBLICATIONS

*J. Am. Chem. Soc.*, vol. 104, No. 24, "Epimerization of Aldoses by Molybdate Involving Novel Rearrangement of the Carbon Skeleton", pp. 6764–6769, 1982.

*Primary Examiner*—H. M. S. Sneed
*Assistant Examiner*—Chung K. Pak
*Attorney, Agent, or Firm*—Oblon, Fisher, Spivak, McClelland & Maier

[57] ABSTRACT

Pentoses and hexoses are epimerized by heating sugar dissolved in a solvent in the presence of a molybdenum(VI) compound, by an improved process in which, for the preparation of a sugar having cis OH groups in the 2- or 3-position, of the formula Ia or Ib $$\begin{array}{cc}
\text{CHO} & \text{CHO} \\
| & | \\
\text{HC}-\text{OH} & \text{HO}-\text{CH} \\
| & | \\
\text{HC}-\text{OH} & \text{HO}-\text{CH} \\
| & | \\
\text{R} & \text{R} \\
\text{(Ia)} & \text{(Ib)}
\end{array}$$

where R is one of the radicals $$\begin{array}{ccc}
| & | & | \\
\text{HC}-\text{OH} & \text{HC}-\text{OH} & \text{HO}-\text{CH} \\
| & | & | \\
\text{CH}_2\text{OH} & \text{HC}-\text{OH} \text{ and } & \text{HC}-\text{OH} \\
 & | & | \\
 & \text{CH}_2\text{OH} & \text{CH}_2\text{OH}
\end{array}$$

a homogeneous solution of the corresponding sugar of the formula IIa or IIb $$\begin{array}{cc}
\text{CHO} & \text{CHO} \\
| & | \\
\text{HO}-\text{CH} & \text{HC}-\text{OH} \\
| & | \\
\text{HC}-\text{OH} & \text{HO}-\text{CH} \\
| & | \\
\text{R} & \text{R} \\
\text{(IIa)} & \text{(IIb)}
\end{array}$$

is heated to 75°–100° C. in the presence of from 30 to 200 mol %, based on sugar used, of a metal salt of the formula (III)

$$\text{MeX}_2 \quad \text{(III)}$$

where Me is Mg, Ca, Sr, Ba or Zn and X is Cl or Br, which may or may not contain water of crystallization, and in the presence of from 2 to 20 mol %, based on the sugar used, of a molybdenum(VI) compound.

The process is particularly important for the preparation of D-ribose, which is required as an intermediate for vitamin B$_2$.

13 Claims, No Drawings

EPIMERIZATION OF SUGARS, IN PARTICULAR OF D-ARABINOSE TO D-RIBOSE

The present invention relates to an improved process for the epimerization of sugars having trans OH groups in the 2- and 3-position of the sugar. This process is particularly important for the preparation of D-ribose by epimerization of D-arabinose, D-ribose being required for the synthesis of vitamin $B_2$.

It is known that D-ribose can be prepared by extraction from natural substances, by fermentation of a microorganism or by chemical synthesis from furan or glucose. However, all these processes are complicated and have a low yield.

D-Ribose was generally prepared industrially by a process in which D-glucose was oxidized with oxygen in an aqueous alkali solution to form D-arabonic acid, which was isolated in the form of a metal salt, e.g. the mercurial zinc salt, and lactonized to give D-ribonolactone, and the latter is reduced with sodium amalgam to D-ribose. Heating D-arabonic acid in an aqueous alkali solution gives a mixture in which the equilibrium ratio of D-arabonic acid to D-ribonic acid is 70:30. In this procedure, it is impossible to obtain a mixture containing more than 30% of D-ribonic acid. Moreover, the use of large amounts of mercury for the amalgam reduction presents difficulties in the process.

Bilik et al. reported that various saccharides could be epimerized in aqueous solution in the presence of a molybdic acid catalyst, including the epimerization of L-arabinose to L-ribose (cf. Czechoslovak Pat. No. 149,472; Chemical Abstracts 81, 78 189 K).

On the basis of this knowledge, a process was developed in which D-gluconic acid was oxidized to D-arabinose instead of to D-arabonic acid. Hypochlorite was used as the oxidizing agent. D-Arabinose is then epimerized in aqueous solution in the presence of a molybdenum catalyst to give D-ribose (cf. Japanese Preliminary Published Application No. 164,699, 1980 and European Pat. No. 20,959 and U.S. Pat. No. 4,355,158). This process achieves an epimerization ratio (proportion of ribose in an equilibrium mixture) of only about 25%. Nevertheless, this process is superior to that described above, since no mercury is used here and fewer steps are required. In one version of the process, a major part of the arabinose is isolated in crystalline form and recycled to the epimerization. To facilitate separation of the molybdic acid from the epimerization solution, the use of a molybdic acid-carrying ion exchanger resin instead of molybdic acid (cf. Japanese Patent Publication No. 40 700/1981) or the use of a molybdic acid-carrying ion exchanger fiber (cf. Japanese Preliminary Published Application No. 76 894/1980) has been described. The epimerization ratio of D-arabinose to D-ribose is 69.4:30.6. Japanese Preliminary Published Application No. 54 197/1982 discloses an epimerization ratio of 27.2% of D-ribose.

It is also known that, by heating L-arabinose in dimethylformamide in the presence of dioxobis-(2,4-pentadionato-0,0')-molybdenum (VI), 36% of the L-arabinose is epimerized to L-ribose (cf. Abe et al. in Chemical and Pharmaceutical Bulletin, 28 (1980), 1324).

Further improvement in the ribose selectivity is achieved by adding boron compounds in a 2-fold to 3-fold molar amount to the epimerization mixture (cf. JP-OS No. 1,890,976/83, JP-OS No. 223,187/83 and German Laid-Open Application No. DOS 3,437,571).

This gave an epimerization equilibrium of about 60% in aqueous solution and up to 94% in nonaqueous solution. The disadvantage of this process is that the boric acid cannot be separated off to an extent acceptable for vitamin $B_2$ preparation without ribose and arabinose also being removed, i.e. the yield of total sugars decreases sharply with each measure to separate off the boric acid. Moreover, the unconverted arabinose in the boric acid-containing solution cannot be separated from ribose and reused.

It is an object of the present invention to improve the process for the preparation of a D-ribose-containing solution from a D-arabinose-containing solution by epimerization in the presence of a molybdenum(VI) compound in such a way that the equilibrium in the epimerization reaction is shifted substantially toward ribose without the sugar yield being greatly reduced as a result of separating off the auxiliary. It is a further object of the present invention to provide an epimerization process which is free of the disadvantages of the prior art and also suitable for the epimerization of other pentoses and hexoses.

We have found that these objects are achieved and that, surprisingly, the equilibrium in the epimerization of arabinose to ribose in the presence of a molybdenum(VI). compound can be shifted substantially toward ribose, if the epimerization of the arabinose solution is additionally carried out in the presence of from 30 to 200 mol %, based on arabinose used, of the bromide or chloride of an alkaline earth metal or of zinc. Another surprising feature here was that the molybdenum(VI) compound required as the catalyst is not precipitated as the sparingly soluble molybdate during the epimerization, despite the large excess of alkaline earth metal or zinc ions, but the metal salts and the molybdenum compound can be separated off virtually quantitatively as a sparingly soluble precipitate after the epimerization by adding sodium or ammonium carbonate, without sugar too being precipitated.

The addition of this metal salt also produces a shift in the equilibrium in the epimerization reaction when other pentoses and hexoses are epimerized, the shift in each case being toward the sugar having the larger number of cis OH groups. This indicates that the shift in the equilibrium in the epimerization reaction is essentially attributable to the formation of sugar/metal salt complexes. Fortunately, the complexes are not very stable, so that the metal salts are subsequently easy to separate off.

The present invention therefore relates to an improved process for the epimerization of pentoses and hexoses by heating sugar dissolved in a solvent in the presence of a molybdenum(VI) compound, wherein, for the preparation of a sugar having cis OH groups in the 2- and 3-position, of the formula Ia or Ib

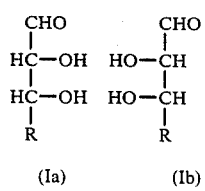

where R is one of the radicals

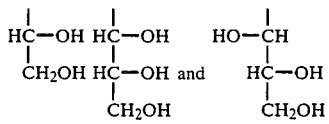

a homogeneous solution of the corresponding sugar of the formula IIa or IIb

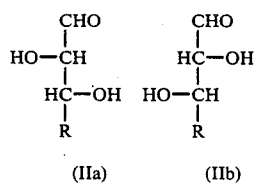

is heated to 75°–100° C. in the presence of from 30 to 200, preferably from 80 to 120, mol %, based on the sugar used, of a metal salt of the formula (III)

$$MeX_2 \quad (III)$$

where Me is Mg, Ca, Sr, Ba or Zn and X is Cl or Br, which may or may not contain water of crystallization, and in the presence of from 2 to 20, preferably from 8 to 12, mol %, based on the sugar used, of a molybdenum(VI) compound.

The process can be carried out particularly advantageously if the molybdenum catalyst and the metal salt are precipitated together as a sparingly soluble precipitate from the reaction solution obtained in the epimerization, by adding an alkali metal or ammonium carbonate, the neutal salts (predominantly alkali metal or ammonium chlorides) are removed in a conventional manner by electrodialysis and the unconverted sugar is then crystallized out in a conventional manner, or if the resulting crude reaction mixture in the form of an aqueous solution is separated into fractions by chromatography directly over a highly acidic cationic exchanger whose resin is laden with the metal ions used in the epimerization. The particularly advantageous aspect of the chromatographic separation is that the molybdenum compound can be precipitated virtually quantitatively as molybdate from the fractions containing it, by precipitation with NaOH or NH4OH, and can be recovered in this way and reused. The molybdenum compound and the added MeCl2 can be precipitated together by using Na2CO3 or (NH4)2CO3 solution. Both measures make it possible to keep pollution of the waste-waters with heavy metals to a minimum. The precipitate which separates out with the carbonates can readily be worked up again in situ using 50–200 mol % of the corresponding acid HX (X=Cl or Br), and the metals can be reused in the epimerization.

The novel process is very particularly important when an arabinose-containing solution is epimerized in order to prepare a solution predominantly containing D-dribose, since on the one hand ribose is a particularly valuable sugar and, on the other hand, the effect on the equilibrium of epimerization is particularly great in this epimerization reaction.

The present invention therefore furthermore relates to a process for the preparation of a solution predominantly containing D-ribose or of pure ribose by epimerization of the D-arabinose-containing solution in the presence of a molybdenum(VI) compound at elevated temperatures, wherein the epimerization is carried out in the presence of from 30 to 200 mol %, based on the D-arabinose used, of a metal salt of the formula III $$MeX_2 \quad (III)$$

where Me is Mg, Ca, Sr, Ba or Zn, preferably Ca or Sr, and X is Cl or Br, which may or may not contain water of crystallization, and the molybdenum catalyst and the metal salt are separated off as a sparingly soluble precipitate from the resulting reaction solution by adding an alkali metal or ammonium carbonate, or the reaction solution obtained in the epimerization, in the form of an aqueous solution, is separated into fractions by chromatography directly over a highly acidic cation exchanger whose resin is laden with the metal ions used in the epimerization. following epimerization equilibria:

| | |
|---|---|
| arabinose (IIa)→ribose (Ia) | (1) |
| xylose (IIb)→lyxose (Ib) | (2) |
| glucose (IIb)→mannose (Ib) | (3) |
| galactose (IIb)→talose (Ib) | (4) |
| altrose (IIa)→allose (Ia) | (5) |
| idose (IIa)→gulose (Ia) | (6) | the epimerization of altrose and idose being less important, since these sugars themselves are not readily accessible.

Suitable metals salts of the formula III are the chlorides and bromides of alkaline earth metals and zinc. The chlorides are preferred. Calcium and strontium salts, in particular calcium chloride and strontium chloride, are very particularly suitable. It is important that the salts are dissolved in the epimerization mixture to give a homogeneous solution.

The best known solvent for salts is water. Where water is used as the solvent, for example for the epimerization of arabinose, a ribose selectivity of up to 45% is obtained. If a nonaqueous solvent is concomitantly used, the ribose selectivity is even further improved, a selectivity of up to 75% being obtained. Among the solvents known for such polymerization reactions, the only suitable ones are those in which the sugar/metal salt/molybdate system dissolves to give a homogeneous solution. Particularly suitable solvents are methanol, ethanol, ethylene glycol and ethylene glycol monomethyl ether, preferably ethanol, if necessary as a mixture with water. The amount of water to be added to the solvent depends, inter alia, on the type of metal salt. Where magnesium chloride is used as the metal salt and ethanol as the solvent, it is possible, for example, completely to dispense with the addition of water. On the other hand, the ethanol must contain about 5–25% by weight of water when calcium chloride or strontium chloride is used, and even as much as 50% when barium chloride is used. The amount of solvent should not exceed from 5 to 20 times the amount of arabinose used. Thus, in the novel process, solutions which contain the metal halides in concentrations of about 5–40, preferably 10–20, % by weight are generally employed. It was surprising that such amounts of salts dissolve in the water-containing organic solvents.

Suitable molybdenum(VI) compounds for the novel polymerization of the compounds known for this purpose, such as molybdenum trioxide, molybdic acid, ammonium molybdate, potassium molybdate, sodium molybdate, calcium molybdate and acetylacetone molybdate. Molybdic acid, ammonium molybdate and calcium molybdate are preferred. These molybdenum compounds are used in an amount of from 2 to 20, preferably about 10, mol %, based on the sugar used.

It was surprising that no molybdate is precipitated from the reaction solution, although the metal halide III is present in up to a 20-fold molar excess, based on $H_2MoO_4$.

The optimum pH for the epimerization has already been stated as 2–4 by Bilik. Where roughly equimolar amounts of $CaCl_2.6H_2O$ and arabinose in 95:5 ethanol/water water are used, as is preferred according to the invention, the reaction mixture is already at an optimum pH. If a pH correction is necessary, it can readily be made with $NH_3$.

The reaction can be carried out by refluxing if a solvent having a boiling point of less than 90° C. is used, or at 78°–95° C. if the solvent has a boiling point of 78° C. or higher. The reaction can be carried out under atmospheric pressure, or under slightly superatmospheric pressure if the solvent has a boiling point of less than 78° C. The reaction time is from 60 to 180 minutes.

The D-ribose-containing solution prepared according to the invention contains, in addition to D-ribose and D-arabinose, very small amounts of D-xylose and D-lyxose, a molybdic acid ion and $MeX_2$. It can also contain ions and byproducts resulting from the reaction of solvents and materials used.

Surprisingly, the metal salts and the molybdenum compound can be separated off together as a sparingly soluble precipitate from this reaction mixture by adding an alkali metal or ammonium carbonate, without significant amounts of sugars being precipitated too. The precipitate comprises a mixture of carbonates and molybdates of the divalent metals used. It can be dissolved in HCl and reused for the epimerization.

The alkali metal or ammonium carbonate is generally used in slightly less than equimolar amounts, ie. about 0.9 mole, based on the metal salt of the formula III employed. The sum of the molar amounts of carbonate and molybdate should correspond roughly to the molar amounts of the metal salt III to be precipitated.

In addition to the sugars, the filtrate also contains neutral salts (predominantly alkali metal or ammonium chlorides). The latter can very advantageously be separated off by electrodialysis of a predominantly aqueous reaction solution. Commercial electrodialysis apparatuses are used for this purpose.

After the neutral salts have been removed, the unconverted arabinose can be substantially crystallized out in a conventional manner, for example by evaporation and the addition of a lower alcohol, with the result that a ribose oil of not less than 90% strength is obtained and can be used as such for further processing to vitamin $B_2$.

We have furthermore found that the crude reaction mixture obtained in the epimerization can, in the form of an aqueous solution, be very advantageously separated into fractions by chromatography over a highly acidic cation exchanger whose resin is laden with the metal ions used in the epimerization. It was surprising that the molybdenum compound too can be quantitatively separated off on the $Me^{2+}$-laden cation exchanger without a sparingly soluble $MeMoO_4$ forming on the exchanger resin. In the prior art, the molybdenum compound was separated from the reaction mixture with the aid of an anion exchanger, before the product mixture was separated by means of a $Ca^{2+}$-laden cation exchanger (cf. Japanese Preliminary Published Application No. 57 054/197). If the epimerization is carried out in aqueous solution, the crude reaction solution can be chromatographed directly. If it is carried out in an organic solvent, the latter must first be replaced with water. By chromatographic separation of this type, it is possible, for example, to separate the mixture obtained in the epimerization of arabinose into the following fractions:

1st fraction: containing $MeX_2$, molybdate and by-products 2nd fraction: containing arabinose, $MeX_2$ and molybdate 3rd fraction: containing ribose (>99%).

From fraction 1, the molybdenum compound can be precipitated as a sparingly soluble molybdate (Me-$MoO_4$) using an alkali metal or ammonium hydroxide, or can be precipitated together with the alkaline earth metal or zinc cations as a sparingly soluble molybdate/carbonate mixture by means of an alkali metal or ammonium carbonate. Not less than 97% of the molybdenum(VI) compound is precipitated, and this compound can readily be converted back to the original, catalytically active form by treatment with dilute HCl solution.

After being evaporated down, fraction 2 can be recycled directly to the epimerization.

Fraction 3 contains pure ribose which can be further processed as a solution or isolated in a conventional manner as pure ribose.

In the case of a fairly high throughput through the cationic exchanger, a further fraction which contains arabinose mixed with ribose can occur. This fraction too, after being evaporated down, can be recycled to the epimerization or, in the case of fairly high ribose contents, can be freed from arabinose by evaporating down and treatment with an alcohol. The optimum throughput through the exchanger can readily be determined in each case by preliminary experiments.

For the chromatographic separation, a commercial, highly acidic cation exchanger of the polystyrene/divinylbenzene type, containing from 4 to 8% of divinylbenzene, is generally used. It should have a very small particle diameter. An exchanger resin having a particle size of from 200 to 400 mesh, from 100 to 200 mesh or from 50 to 100 mesh is preferably used. Specific examples are commercial, highly acidic cation exchangers such as Dowex 50W-X4, Dowex 50W-X8, Lewatite TSW 40, Amberlite-CG-120 II and Mitsubishi MCI gel CK08P.

Using the novel process, it is possible to convert certain pentoses and hexoses, with a very high degree of epimerization, to the corresponding sugar having a larger number of cis OH groups. Both the sugars and the molybdenum(VI) catalyst and, if desired, also the concomitantly used metal salts can be recovered virtually quantitatively.

Particularly noteworthy advantages of the invention are the following:

(a) By adding $MeX_2$, the equilibrium in the polymerization reaction is shifted in the desired direction.
(b) The metal salts $MeX_2$ are very cheap, in particular calcium chloride, which is especially effective.
(c) The added metal salt can be separated off after the epimerization, without loss of sugar.

(d) During the chromatographic separation, the metal salt MeX$_2$ constantly keeps the ion exchanger optimally laden with Me$^{2+}$ ions for the separation.
(e) The excess of MeX$_2$ permits quantitative recovery of the molybdenum compound.
(f) Both in the separation of the metal salts MeX$_2$ and in that of the catalyst, no significant sugar losses occur.

The novel process has the following advantages, particularly for the industrially particularly important epimerization of arabinose to ribose:

Ribose is obtained in a selectivity of 75% in a reaction solution from which (a) pure D-ribose and unconverted D-arabinose can be obtained separately and without loss in one process step, and the molybdenum catalyst and the metal salt are obtained in separate fractions, from which, if desired, either the catalyst alone or the catalyst together with the metal salt can be separated off and reused and (b) the metal salt and the catalyst can be separated off quantitatively by a simple precipitation and can therefore be reused, and furthermore, after precipitation of arabinose, a ribose solution of not less than 90% strength can be obtained.

Both the solution prepared as described in (a) and that prepared as described in (b) are suitable for the preparation of pure N-D-ribityl-3,4-xylidene (ribamine), an intermediate of vitamin B$_2$ (riboflavin). When ribose worked up according to (a) is used, the maximum yield of pure ribamine is obtained (88–90%).

The ratio of the pentoses was determined by HPLC after precipitation of the metal salts III with concentrated Na$_2$CO$_3$ solution (carbohydrates (Latek), 88:12 acetonitrile/H$_2$O by 0.5% of H$_3$PO$_4$, 1.5 ml/min, 2 columns in series). Elution is carried out in the following sequence:

| | |
|---|---|
| ribose | 8.3 min |
| lyxose | 10.4 min |
| xylose | 11.4 min |
| arabinose | 12.7 min |

The reducing sugars were determined via reduction of CuSO$_4$ to CuO in citric acid-containing, alkaline solution, followed by iodometric determination.

The alkaline earth metals or zinc ions were determined by the complexometric method, and Mo by atomic absorption spectroscopy.

EXAMPLE 1

A solution of 15 g of arabinose, 40.6 g of MgCl$_2$.6H$_2$O and 1.8 g of ammonium molybdate in 80 ml of ethanol was refluxed for 3 hours. HPLC analysis gave the following result:

| | |
|---|---|
| ribose | 62% |
| lyxose | not detectable |
| xylose | not detectable |
| arabinose | 38% |

EXAMPLE 2

A solution of 15 g of arabinose, 27 g of SrCl$_2$.6H$_2$O and 1.8 g of ammonium molybdate in a mixture of 80 ml of ethanol and 10 ml of water was refluxed for 3 hours. After the mixture had cooled to 40° C., saturated Na$_2$CO$_3$ solution was added, the mixture was stirred overnight and the precipitate was filtered off and washed thoroughy with H$_2$O. In the resulting filtrate, the following were determined by HPLC analysis:

| | |
|---|---|
| ribose | 70.9% |
| arabinose | 29.1% |
| xylose | not detectable |
| lyxose | not detectable. |

EXAMPLE 3

A solution of 15 g of arabinose, 44 g of CaCl$_2$.6H$_2$O and 1.7 g of molybdic acid in 80 ml of ethanol and 20 ml of water was brought to pH 3.0 with NH$_3$ and then refluxed for 3 hours. After the mixture had cooled, 21.2 g of Na$_2$CO$_3$ and 45 g of H$_2$O were added. The mixture was stirred overnight, and the precipitate was filtered off under suction and washed thoroughly with water. 21.5 g of CaCO$_3$.CaMoO$_4$ were obtained, the yield of reducing sugar being 95% of theory. HPLC analysis of the sugar solution gave the following result:

| | |
|---|---|
| ribose | 68% |
| lyxose | 0.6% |
| arabinose | 31.4% |
| xylose | not detectable |

EXAMPLE 4

A solution 15 g of arabinose, 21.9 g of CaCl$_2$.6H$_2$O and 1.7 g of molybdic acid in 80 ml of glycol monomethyl ester and 20 ml of H$_2$O was brought to a pH of about 3.0 with NH$_3$ and stirred for 60 minutes at 90° C. After precipitation with (NH$_4$)$_2$CO$_3$, the following were obtained, the total yield of reducing sugars being 96%:

| | |
|---|---|
| ribose | 65% |
| lyxose | 0,8% |
| arabinose | 34.2% |
| xylose | not detectable. |

EXAMPLE 5

A solution of 15 g of arabinose, 35.32 g of SrCl$_2$.6H$_2$O and 1.8 g of ammonium molybdate in a mixture of 20 ml of water and 80 ml of ethanol was refluxed for 3 hours. After the mixture had been cooled, the ratio of the pentoses was determined by HPLC.

| | |
|---|---|
| ribose: | 69.6% |
| lyxose: | 0.3% |
| arabinose: | 30.1% |

EXAMPLE 6

A stirred solution of 30 g of arabinose, 44 g of CaCl$_2$.6H$_2$O and 3.6 g of ammonium molybdate in 190 ml of ethanol and 8 ml of H$_2$O was refluxed for 3 hours. The mixture was then cooled to 50° C. and 50% of the ethanol was replaced with H$_2$O. The yield of reducing sugar was 95%.

| | |
|---|---|
| ribose | 75.3% |

-continued

| | |
|---|---|
| lyxose | 0.4% |
| arabinose | 24.3% |

After chromatography over a highly acidic ion exchanger (Dowex 50W-X4) in the $Ca^{2+}$ form, 4 fractions were obtained, and the ribose/arabinose mixed fraction (fraction 3) was chromatographed again after being evaporated down.

| Fraction 1 | |
|---|---|
| $CaCl_2$ | 63% |
| Mo | 55% |
| byproducts | |

Fraction 1 was brought to a pH of about 8.5–9 with NAOH, $NH_3$ or KOH and heated at 100° C. for 1 hour. The precipitate was filtered off. 2.2 g (~98%) of $CaMoO_4$ were obtained.

| Fraction 2 | |
|---|---|
| lyxose | 1.6% |
| xylose | 0.4% |
| arabinose | 96.9% |
| ribose | 1.0% |
| | 7.1 g of reducing sugar |
| | = 23.7% based on arabinose used |
| Ca | 38% |
| Mo | 45% |

Fraction 2 was evaporated down and used in Example 7.

| Fraction 4 | |
|---|---|
| ribose | 99.7% |
| arabinose | 0.3% |
| | 21.4 g of reducing sugar |
| | = 71.2%, based on arabinose used. |

EXAMPLE 7

(a) A solution of 23 g of arabinose and 7 g of the sugar from fraction 2 of Example 6, 28 g of $CaCl_2.6H_2O$ and about 12 g of $CaCl_2.6H_2O$ from fraction 2 of Example 6, and 2.5 g of $CaMoO_4$, dissolved in 15 ml of 1N HCl, and about 1.6 g of ammonium molybdate from fraction 3 of Example 6 in 190 ml of ethanol was refluxed for 3 hours. The yield of reducing sugars was 93%, the composition being as follows:

| | |
|---|---|
| ribose | 68.5% |
| lyxose | 0.9% |
| xylose | 0.2% |
| arabinose | 30.4%. |

The mixture was worked up similarly to Example 6. 19 g of ribose (99.8% pure) were obtained, corresponding to a total yield of 63.4%.

(b) Fraction 1 comprised about 520 g, containing 11 millimoles of molybdate. 12 millimoles of 50% strength aqueous NaOH were added to this fraction, and the mixture was refluxed for 1 hour. When the mixture had cooled, the resulting precipitate was filtered off and dried. 2.38 g of $CaMoO_4$ were obtained (molybdenum content=44.2%). This corresponded to a separation of 99.7% of the theoretical amount of Mo. The residual molybdenum content in the filter was less than 1 ppm.

EXAMPLE 8

15 ml of aqueous 1M HCl were added to 2.25 g of the $CaMoO_4$ obtained as described in Example 7b, and the mixture was refluxed for 30 minutes. 15 g of arabinose, 14.1 g of $CaCl_2.H_2O$ and 90 ml of ethanol were then added to this mixture, and the resulting reaction mixture was refluxed for 3 hours.

Thereafter, 74.9% of ribose and 25.1% of arabinose were obtained, by no lyxose or xylose.

EXAMPLE 9

A stirred solution of 30 g of xylose, 43.8 g of $CaCl_2.6H_2O$ and 3.6 g of ammonium molybdate in 190 ml of ethanol was refluxed for 1 hour and then cooled to 55° C., and the ethanol was distilled off under reduced pressure, 100 ml of water being metered in at the same time. The yield of reducing sugar was 96%; the solution contained 63% of lyxose and 37% of xylose. Subsequent chromatography over Dowex 50W-X4 gave 3 fractions which contained the components described below:
 Fraction 1: Mo(VI) and $CaCl_2$
 Fraction 2: Mo(VI), $CaCl_2$, 87% of xylose and 13% of lyxose (a total of 10 g of reducing sugars)
 Fraction 3: 93% of lyxose and 7% of xylose (a total of 17.8 g of reducing sugars).

EXAMPLE 10

36 g of galactose, 43.8 g of $CaCl_2.6H_2O$ and 3.6 g of ammonium molybdate were dissolved in a mixture of 4 g of water and 190 ml of ethanol, and the solution was refluxed for 3 hours. The ethanol was then distilled off under reduced pressure at 55° C., 100 ml of water being metered in at the same time. The reaction mixture contained 52.2% of unconverted galctose and 47.8% of talose.

Chromatographic separation over Dowex 50W-X4 in the $Ca^{2+}$ form similarly to Example 7 gave 15.1 g of a 99.9% pure talose.

EXAMPLE 11

A solution of 36 g of glucose, 43.8 g of $CaCl_2.6H_2O$ and 3 g of ammonium molybdate in 4 ml of water and 190 ml of ethanol was converted similarly to Example 10. After the mixture had boiled for 3 hours, a glucose/mannose ratio of 45:55 was determined.

EXAMPLE 12

A solution of 150 g of arabinose, 219 g of $CaCl_2.6H_2O$ and 36 g of ammonium molybdate in 900 ml of ethanol and 50 ml of $H_2O$ was refluxed for 3 hours. After the mixture had cooled to 50° C., 300 ml of a 33% strength $Na_2CO_3$ solution were added, the mixture was stirred overnight and the precipitate was filtered off. The major part of the ethanol was distilled off from the filtrate under reduced pressure, and water was added. The neutral salts (essentially NaCl) were removed from the resulting aqueous solution by electrodialysis in a standard electrodialysis laboratory cell comprising 10 desalination units. A salt-free dark yellow solution which contained 138 g of reducing sugar (92%) was obtained. This solution was substantially evaporated down, ethanol was added and the mixture was stirred for 16 hours. The crystals (27 g of a 90:10 arabinose/ribose mixture) were filtered off under suction and washed with ethanol. The filtrate contained:

| | |
|---|---|
| ribose | 91% |
| lyxose | 1% |
| arabinose | 8% |
| Mo | 0.05 mmol |
| $Ca^{2+}$ | not detectable. |

We claim:

1. In a process for the epimerization of pentoses and hexoses by heating sugar dissolved in a solvent in the presence of a molybdenum (VI) compound, the improvement comprising:

preparing a sugar containing cis OH groups in the 2- or 3-position, of the formula Ia or Ib $$\begin{array}{cc} \text{CHO} & \text{CHO} \\ | & | \\ \text{HC—OH} & \text{HO—CH} \\ | & | \\ \text{HC—OH} & \text{HO—CH} \\ | & | \\ \text{R} & \text{R} \\ (\text{Ia}) & (\text{Ib}) \end{array}$$

wherein R is a radical selected from the group consisting of $$\begin{array}{ccc} | & | & | \\ \text{HC—OH} & \text{HC—OH} & \text{HO—CH} \\ | & | & | \\ \text{CH}_2\text{OH} & \text{HC—OH} \text{ and } & \text{HC—OH} \\ & | & | \\ & \text{CH}_2\text{OH} & \text{CH}_2\text{OH} \end{array}$$

by heating a homogeneous solution of the corresponding sugar having trans OH groups in the 2- and 3-position of the sugar, of the formula IIa or IIb $$\begin{array}{cc} \text{CHO} & \text{CHO} \\ | & | \\ \text{HO—CH} & \text{HC—OH} \\ | & | \\ \text{HC—OH} & \text{HO—CH} \\ | & | \\ \text{R} & \text{R} \\ (\text{IIa}) & (\text{IIb}) \end{array}$$

to 75°–100° C. in the presence of from 30 to 200 mol %, based on the sugar used, of a metal salt of the formula (III)

$$MeX_2 \qquad (III)$$

wherein Me is Mg, Ca, Sr, Ba or Zn and X is Cl or Br and in the presence of from 2 to 20 mol %, based on the sugar used, of said molybdenum (VI) compound.

2. The process as claimed in claim 1, wherein the molybdenum compound and the metal salt are separated as a sparingly soluble precipitate from the resulting epimerized product containing solution and unconverted sugar by adding an alkali metal or ammonium carbonate.

3. The process as claimed in claim 2, wherein the unconverted sugar in the epimerized product containing solution is crystallized out after the sparingly soluble precipitate has been separated and the formed alkali metal or ammonium chlorides resulting from the addition of said alkali metal or ammonium carbonate have been removed by electrodialysis.

4. The process as claimed in claim 1, wherein the epimerization is carried out in the presence of about 80–120 mol %, based on sugar used, of the metal salt of the formula III.

5. The process as claimed in claim 1, wherein the epimerization is carried out in the presence of from 8 to 12 mol %, base on the sugar used, of said molybdenum (VI) compound.

6. The process as claimed in claim 1, wherein the epimerization is carried out in the presence of a calcium or strontium salt of the formula III.

7. The process as claimed in claim 1, wherein the epimerization is carried out in the presence of a selected from the group consisting of ethanol and aqueous ethanol containing up to 50% of water.

8. The process as claimed in claim 1 wherein the resulting epimerized product containing solution and unconverted sugar is fractionated by chromatography over a highly acidic cation exchanger whose resin is laden with the metal ions used in the epimerization.

9. The process as claimed in claim 1, wherein said metal salt further contains water of crystallization.

10. A process of the preparation of a solution predominantly containing D-ribose or pure ribose, comprising:

epimerizing D-arabinose in a solution containing the same at an elevated temperature in the presence of from 2 to 20 mol %, based on said arabinose, of a molybdenum (VI) compound and in the presence of from 30 to 200 mol %, based on said arabinose, of a metal salt of the formula III $$MeX_2 \qquad (III)$$

wherein Me is Mg, Ca, Sr, Ba or Zn and X is Cl or Br; and separating said molybdenum compound and said metal salt as a sparingly soluble precipitate from the resulting epimerized product containing solution by adding an alkali metal or ammonium carbonate thereto.

11. The process as claimed in claim 10, wherein said metal salt further contains water of crystallization.

12. A process of the preparation of a solution predominantly containing D-ribose or pure ribose, comprising:

epimerizing D-arabinose in a solution containing the same at an elevated temperature in the presence of from 2 to 20 mol %, based on said arabinose, of a molybdenum (VI) compound and in the presence of from 30 to 200 mol %, based on said arabinose, of a metal salt of the formula III $$MeX_2 \qquad (III)$$

wherein Me is Mg, Ca, Sr, Ba or Zn and X is Cl or Br; and fractionating the resulting epimerized product containing solution by chromatography directly over a highly acidic cation exchanger whose resin is laden with the metal ions used in the epimerization.

13. The process as claimed in claim 12, wherein said metal salt further contains water of crystallization.

* * * * *